(12) United States Patent
Saxena

(10) Patent No.: US 7,585,661 B2
(45) Date of Patent: Sep. 8, 2009

(54) **PROCESS FOR PRODUCING HERBICIDES FROM A FUNGUS *ALTERNARIA ALTERNATA* F.SP. LANTANAE**

(75) Inventor: Sanjai Saxena, New Delhi (IN)

(73) Assignee: National Research Development Corporation, New Delhi (IN)

( * ) Notice: Subject to any disclaimer, the term of this patent is extended or adjusted under 35 U.S.C. 154(b) by 262 days.

(21) Appl. No.: 10/531,846

(22) PCT Filed: Oct. 16, 2002

(86) PCT No.: PCT/IN02/00210

§ 371 (c)(1),
(2), (4) Date: Sep. 28, 2005

(87) PCT Pub. No.: WO2004/034790

PCT Pub. Date: Apr. 29, 2004

(65) Prior Publication Data

US 2006/0142160 A1  Jun. 29, 2006

(51) Int. Cl.
*A01N 63/00* (2006.01)

(52) U.S. Cl. .................................. 435/254.1; 424/93.5

(58) Field of Classification Search .................. None
See application file for complete search history.

(56) References Cited

OTHER PUBLICATIONS

Lawrie et al., Biocontrol Science and Technology, vol. 10, No. 1, Feb. 1, 2000, pp. 81-87(7).*

* cited by examiner

*Primary Examiner*—Irene Marx
(74) *Attorney, Agent, or Firm*—The Webb Law Firm

(57) ABSTRACT

A process for producing herbicides from a fungus *Alternaria alteranata* f.sp. lantanae deposited as a pure culture as MTCC 5432 and ITCC-4896, comprising culturing the fungus in a liquid broth; subjecting the broth to the step of filtration to separate the broth containing phytotoxins from mycelium; extracting the phytotoxins from said broth to obtain the phytotoxins; and subjecting the phytotoxins to chemical characterization.

14 Claims, No Drawings

PROCESS FOR PRODUCING HERBICIDES FROM A FUNGUS *ALTERNARIA ALTERNATA* F.SP. LANTANAE

FIELD OF INVENTION

This invention relates to a process of preparing herbicide from a fungus *Alternaria alternate* f.sp. lantanae and herbicides prepared therefrom. Such a fungus has been deposited on Jul. 25, 2008 at MICROBIAL TYPE CULTURE COLLECTION & GENE BANK (MTCC) Sector 39-A, Chandigarh 160 036, India as a pure culture and has the deposit accession number of MTCC 5432. Previously such fungus was deposited at the Indian Agricultural Research Institute-Division of Plant Pathology, Indian Agriculture Research Institute (IARI), New Delhi 110 012 under the Budapest Treaty as Deposit No. ITCC-4896.

BACKGROUND OF INVENTION

It is generally known that fungus *Alternaria alternate* is present on a host plant. Depending on the species, such a fungus can cause a disease to the host plant, simultaneously, it is known that lantana weed causes damage to agricultural and forestry plants.

As a result of the increasing environmental and health-related caused by the synthetic agrochemicals currently used, suitable and non-hazardous innovative alternatives are being sought. The persistence and long-term toxicity of xenobiotics to non-target organisms, including humans, has generated concern, regarding their further use, and this has necessitated the re-evaluation of synthetic chemicals as a final solution to pest disease management (Stevens 1991). Recently, 2,4-dichlorophenoxyacetic acid has been banned in certain countries because of deleterious effects on farmers (Szmedra 1997).

Weeds are very important crop pests. Herbicides for weed control are the leading type of pesticides in terms of both expenditure and volume used.

Weeds have diverse microorganisms (pathogenic as well as non-pathogenic), and these groups of microorganisms have been neglected for their prospective use as an alternative to synthetic chemicals for sustainable agriculture and forestry.

Bacterial phytotoxins are generally hetero-nuclear in nature and are generally anti-metabolites or hormones and thus lack overall specificity towards plants.

OBJECT OF THE INVENTION

An object of this invention is to process novel herbicides from a fungus *Alternaria alternata* f.sp. lantanae and a process for the preparation thereof.

Another object of this invention is to propose herbicides from a fungus *Alternaria alternata* f.sp. lantanae and a process for the preparation thereof which has suitable herbicidal activity.

In accordance with this invention, the fungus is isolated as a pure culture. Such a culture has been deposited as a culture ITCC 4896 (IARI-India).

The fungus is subjected to the step of incubation at the temperature of 20-30° C. for a period of 5-10 days. The fungus is further cultured in a liquid medium containing modified and a nutrient source such as sucrose. Modified Richard medium is known in the art and comprises potassium nitrate, dihydrogen potassium phosphate, magnesium sulphate and ferric chloride.

The fungus is inoculated into the culture medium. The rate of growth of the fungus is dependent on the concentration of the inoculum. Preferably, 3 to 12 mm disc of 7 days old culture is inoculated into the culture medium. It has been found that the time of incubation substantially increases if the disc is less than 3 mm.

The step of fermentation is preferably carried out for a period of 18 to 30 days, and optimally 21 days, though not limited thereto, and at a temperature of 20 to 30° C. and a pH of 3 to 7. It has been found that the period of incubation substantially increases if the temperature is less than 20° C. If the temperature is more than 30° C., compounds other than the required toxins are produced.

Such a fermented or incubated medium is subjected to the step of filtration to separate the mycelium. From the cell free filtrate or broth. The fermented medium is filtered through seitz filtration unit using a vacuum pump. The filter use is nitro cellulose filter of 0.2 um-1 um mesh size. The broth is a clear solution containing toxins or cell free filtrate. Such a broth is alkaline with a pH 7 to 8.

The ph of such a broth is adjusted to a pH 2 to 3. The pH of the filterate is adjusted between 2-3 using 1-3 ml of an acid such as HCl, $H_2SO_4$orthophosphoric acid for the concentration between 1-4 normal and 1-3 ml for very 1 litre of broth. The broth is then concentrated in vacuum for removal of liquid. Optimally, through not limited thereto, the step of concentration is carried out at a temperature of 35° to 40° C. The concentration is carried out 40 to 60% of original volume to produce a concentrated brown viscons mass.

The next step in the process comprises in the step of solvent extraction of the brown viscons mass using polar or non polar solvents, such as hexane, dichloromethane, benzene or chloroform in the ratio between 1:1-1:15. Preferably, chloroform is employed as the solvent. If required, such a step of extraction may be repeated. The treatment with solvents produces two immiscible layers, namely an oily layer above a solvent layer. By any suitable means, such as a separating funnel the solvent layer is partitioned. The residue or oil layer is tested for phytotoxicity against the host plant and it is found to be active in range of 0.1-10 ppm (w/v) while testing the phytotoxicity. The residue (yellowish brown oily substances) is dissolved in a mixture of water and ethanol in the ratio of 8-12:0.5-2 w/v. Water and ethanol are mixed with each other in the ratio of 1-3:1. Solvent is removed from the residual oil layer by the step of evaporation to produce a concentrate which is yellowish in colour, which is one of the desired compounds having herbicidal activity. Such a step of evaporation is carried out in vacuum at a temperature of 30 to 35° C. to produce a yellow oil residue having a phytotoxic activity, which is then subjected to the step of chemical characterization, comprising the steps of TLLC and HPLLC. The step of chemical characterization comprises in subjecting the residue to the step of transmethylation so as to make it water soluble by dissolving the same into a mixture of methanol, benzene, sulphuric acid mixed in the ratio of 20:10:0.5-1 at temperature of 60-80° C. for a period of 1-2 hours. The solution so obtained is tested and found to be active against the host plant at a concentration of 0.1-10 ppm. The methyl derivatives are purified from the transmethylation solution by using TLC process. The mixture of solvent used in the TLC process comprises chloroform diethylether methanol and distilled water in the ratio of 5-7:1-3:1-3:0.5-1.5.

The purified solution is then subjected to the process of TLC again to obtain the compounds (3 of different retention frequency (RF) values). These compounds are then removed from TLC plate and are dissolved in 10 ml ethanol (90%)

respectively. The solution is then evaporated so as to obtain the residue of the pure compound as follows:
1. Light yellow crystals are of 0.88 RF value and the yield is 75% w/v of the broth taken for this purpose.
2. Orange crystals are of 0.75 RF value and the yield is 18% of the original volume.
3. White powder is of RF value 0.49 and the yield is 5% only.

These compounds are tested for purity by the conventional process of HPLC and are found to be 100% pure. The compounds are also tested for herbicidal activity and are found to be equally effective to kill the weeds like Lantana camara and Parthinium. Subsequently the compounds are subjected to be GC/MS-MS analyses using silicon column number BP10 for finding out the atomic mass unit (AMU).

The results are as follows:

1. RF-0.88 compound the retention time is 4.5 and atomic mass is 297.
2. RF 0.79 compound the retention time is 7.16 and the atomic mass unit is 371.
3. RF 0.49—the retention time is 9.5 and the atomic mass is 445.

The natural compound library search report shows that the compound of the above atomic mass unit's have not been reported and are the novel compounds.

A process for producing herbicidal idiolites from the fungus/infected weeds according to a preferred embodiment is herein described in the following examples:

EXAMPLES 2 gms visually observed infected leaves of the weed plant (lantana camara) were immersed in 10 ml ethanol (60-90%) for 8 seconds and then transferred to 10 ml sodium hydrochloride solution (NaOcl) for 4 minutes and then washed twice with sterile distilled water. The washed leaves were cut into pieces (0.4 mm) and then cut pieces were transferred to 10 ml semisolid neutriant medium of fresh potato dextrose agar mixed with antibiotic (chloroamphenicol) @45 mg/litre. The mixture so obtained was incubated at a temperature of 24° C. for the period of 8 days. The plate containing the pure culture of micro-organisms (named as *Alternaria alterneta* pv lantana) was taken out 4 mm mycelial of the culture of were taken out in the disc form and transferred to a sterile liquid neutriant medium. One disc of the above mentioned size was put into 50 ml of sterile broth/liquid medium. One litre of the broth so obtained was taken for the fermentation process. The broth was again incubated at a temperature of 24° C. for a period of 20 days and was subsequently filtered to get cell free filterate (CFF).

The pH of the filterate was adjusted at 2.8 using hydrochloric acid (1 normal) @1.5 ml/500 ml of the filterate (CFF). The filterate was then concentrated by evaporation at a temperature of 40° C. to half of the original volume. The concentrated filterate was subjected to the step of solvent extraction for the recovery of the reactive compounds (oily yellowish brown liquid) which was found to be active to kill the host weed. The oily yellowish brown liquid was transmethylated using a mixture of benzene, methanol and sulphuric acid in the ratio of 20:10:0.4 for one hour. The transmethylated derivatives were purified by using TLC process. These compounds were observed under UV with retention frequency (rf) of 0.88, 0.75 and 0.49 respectively. The derivatives of the above retention frequency were removed and were mixed with 10 ml methanol (90%) separately and were subsequently flashed evaporated. The compound of retention frequency 0.88 was yellowish crystals. The compound of retention frequency 0.75 was orange crystals and the compound of 0.49 retention frequency was a white powder. All the above compounds were found active to kill the host tree/weed.

The tests were conducted to find out the purity of the above compounds and it was established that the compounds were pure. The compounds were also subjected to GC-MS/MS analyses and the following results were found:

| Compounds | Retention time in minutes | Mass |
|---|---|---|
| 0.88 RF | 4.53 | 297 |
| 0.75 RF | 7.12 | 371 |
| 0.49 RF | 9.12 | 453 |

It was found that all the above mentioned compounds were active to kill the host plant/weed jointly and separately.

Reference is now made to oily phase. The oil layer is subjectyed to a plurality of steps of extraction with a fresh solvent each time, the fractions from each extraction are combined. Residual solvent is removed by evaporation in vacuum and preferably at temperature of 30 to 35° C. for 10to 25 minutes. Such a concentrate is then subjected to a plurality of steps of extraction with another solvent, such as ethyl acetate, and the fractions are combined, which yield two other compounds which exhibit herbicidal activity.

The step of extraction produces a solvent layer and an oily residue. The solvent layer contains two other active compounds with phytotoxic activity. The solvent layer is subjected to evaporation in vacuo at a temperature of 30 to 35° C. to produce an oily residue, which is then subjected to chemical characterization by the steps of TLLC and HPLLC.

Reference is now made to mycelium obtained from the step of filtration. Such a mycelium is ground, formulated as a water spray for control of weeds.

I claim:

1. A process for producing herbicides from the fungus *Alternaria alternata* f.sp. lantanae deposited as a pure culture as ITCC-4896, comprising culturing the fungus in a liquid broth; subjecting the broth to the step of filtration to separate the broth containing phytotoxins from mycelium; extracting the phytotoxins from said broth to obtain the phytotoxins; and subjecting the phytotoxins to chemical characterization.

2. The process as claimed in claim 1, wherein the subjecting step is performed aseptically.

3. The process as claimed in claim 2, wherein the inoculum is inoculated into a liquid medium and growth is allowed for a period of 20 to 30 days under static conditions.

4. The process as claimed in claim 2, wherein the inoculum have a disc size of 3 to 12 mm.

5. The process as claimed in claim 2, wherein the inoculum have a disc size of 5 to 8 mm.

6. The process as claimed in claim 5, wherein the inoculated broth after growth is subjected to filtration under vacuum to separate the mycelium from cell free filtrate.

7. The process as claimed in claim 6, wherein the pH of the cell free filtrate is adjusted to a pH 2 to 3 and concentrated to 40-60% of original volume under vacuum to produce a concentrated brown viscous mass.

8. The process as claimed in claim 7, wherein the brown viscous mass is treated with solvents, thereby producing a solvent layer and an oily layer.

9. The process as claimed in claim 8, wherein the solvent layer containing a first active compound is evaporated under vacuum at a temperature of 30 to 35° C. to produce a yellowish oily residue having phytotoxic activity and subjecting said residue to chemical characterization.

10. The process as claimed in claim 8, wherein the oily layer is subjected to subsequent extraction by a solvent, to produce another solvent layer and another oily residue.

11. The process as claimed in claim 10, further comprising the steps of evaporating the solvent layer at a temperature of 30 to 35° C. under a vacuum to produce a residue containing two other active compounds with phytotoxic activity, which are subjected to chemical characterization.

12. The process as claimed in claim 8, wherein the solvent used in solvent extraction is a polar solvent.

13. The process as claimed in claim 8, wherein the solvent used in solvent extraction is chloroform.

14. The process as claimed in claim 6, wherein the mycelium is ground and formulated as a water spray for a weedicide.

* * * * *

UNITED STATES PATENT AND TRADEMARK OFFICE
CERTIFICATE OF CORRECTION

| | | |
|---|---|---|
| PATENT NO. | : 7,585,661 B2 | Page 1 of 1 |
| APPLICATION NO. | : 10/531846 | |
| DATED | : September 8, 2009 | |
| INVENTOR(S) | : Saxena | |

It is certified that error appears in the above-identified patent and that said Letters Patent is hereby corrected as shown below:

Title page, Item (54) line 2 of the title, *"ALTERNARIA ALTERNATA"*
should read:   -- *ALTERNARIA ALTERANATA* --

Column 4, Line 38, Claim 1, *"Alternaria alternata"* should read
-- *Alternaria alteranata* --

Signed and Sealed this

Twelfth Day of January, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,585,661 B2 | Page 1 of 1 |
| APPLICATION NO. | : 10/531846 | |
| DATED | : September 8, 2009 | |
| INVENTOR(S) | : Saxena | |

It is certified that error appears in the above-identified patent and that said Letters Patent is hereby corrected as shown below:

<u>Title page</u>, Item (54) line 2 and at Column 1, line 2, of the title, "*ALTERNARIA ALTERNATA*"
should read:  -- *ALTERNARIA ALTERANATA* --

<u>Column 4</u>, Line 38, Claim 1, "*Alternaria alternata*" should read
-- *Alternaria alteranata* --

This certificate supersedes the Certificate of Correction issued January 12, 2010.

Signed and Sealed this

Second Day of February, 2010

David J. Kappos
*Director of the United States Patent and Trademark Office*

UNITED STATES PATENT AND TRADEMARK OFFICE
CERTIFICATE OF CORRECTION

PATENT NO.       : 7,585,661 B2                                    Page 1 of 1
APPLICATION NO. : 10/531846
DATED            : September 8, 2009
INVENTOR(S)      : Sanjai Saxena It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 548 days.

Signed and Sealed this

Fourteenth Day of September, 2010

David J. Kappos
*Director of the United States Patent and Trademark Office*